(12) United States Patent
Lautenschläger

(10) Patent No.: US 8,077,947 B2
(45) Date of Patent: Dec. 13, 2011

(54) METHOD FOR DETERMINING AN OPTIMAL OUTPUT OF AN ABLATION CATHETER FOR A MYOCARDIAL ABLATION IN A PATIENT AND ASSOCIATED MEDICAL APPARATUS

(75) Inventor: Stefan Lautenschläger, Hausen (DE)

(73) Assignee: Siemens Aktiengesellschaft, Munich (DE)

( * ) Notice: Subject to any disclaimer, the term of this patent is extended or adjusted under 35 U.S.C. 154(b) by 848 days.

(21) Appl. No.: 12/214,208

(22) Filed: Jun. 17, 2008

(65) Prior Publication Data

US 2008/0317319 A1      Dec. 25, 2008

(30) Foreign Application Priority Data

Jun. 19, 2007   (DE) .......................... 10 2007 028 115

(51) Int. Cl.
*G06K 9/00*           (2006.01)

(52) U.S. Cl. .................... 382/128; 382/154; 600/424

(58) Field of Classification Search .......... 382/128–132, 382/154; 600/423–429
See application file for complete search history.

(56) References Cited

U.S. PATENT DOCUMENTS

| | | | |
|---|---|---|---|
| 7,327,872 B2* | 2/2008 | Vaillant et al. ................ | 382/154 |
| 7,565,190 B2* | 7/2009 | Okerlund et al. ............ | 600/426 |
| 7,610,078 B2* | 10/2009 | Willis ........................... | 600/424 |
| 7,801,342 B2* | 9/2010 | Boese et al. ................... | 382/128 |
| 2006/0078195 A1* | 4/2006 | Vaillant et al. ................ | 382/154 |
| 2008/0075343 A1* | 3/2008 | John et al. ..................... | 382/131 |
| 2009/0148012 A1* | 6/2009 | Altmann et al. .............. | 382/128 |

FOREIGN PATENT DOCUMENTS

| | | |
|---|---|---|
| DE | 102005045363 A1 | 4/2007 |
| EP | 0873722 A1 | 10/1998 |
| EP | 1720038 A2 | 11/2006 |

* cited by examiner

*Primary Examiner* — Jingge Wu

(57) ABSTRACT

The invention relates to a method for determining an optimal output of an ablation catheter for a myocardial ablation in a patient with the following steps: creation of at least one at least three-dimensional image recording of an ablation region provided for the myocardial ablation using at least one image recording apparatus; at least partial segmentation of the recorded ablation region to obtain segmentation information using a computation apparatus; at least partial determination from the segmentation information of the location-dependent thickness of the myocardium in the ablation region by the computation apparatus; and determination of the optimal output of the ablation catheter, in particular by the computation apparatus or a separate computation apparatus of an ablation catheter system, as a function of the determined myocardium thickness.

15 Claims, 3 Drawing Sheets

METHOD FOR DETERMINING AN OPTIMAL OUTPUT OF AN ABLATION CATHETER FOR A MYOCARDIAL ABLATION IN A PATIENT AND ASSOCIATED MEDICAL APPARATUS

CROSS REFERENCE TO RELATED APPLICATIONS

This application claims priority of German application No. 10 2007 028 115.5 filed Jun. 19, 2007, which is incorporated by reference herein in its entirety.

FIELD OF THE INVENTION

The invention relates to a method for determining an optimal output of an ablation catheter for a myocardial ablation in a patient and associated medical apparatus.

BACKGROUND OF THE INVENTION

According to current studies the number of cardiological diseases is constantly increasing. One typical pathological finding here is so-called ventricular fibrillation or flutter. Abnormalities of pathological origin here cause defective neuron pathways in the ventricle with the result that the heart beats in an uncontrolled manner (too frequently). This is associated with a reduction in the time available to fill the ventricle, so cardiac performance is greatly reduced.

Ventricular fibrillation or flutter gives rise to acute complaints such as chest pain and reduced capability, etc. There is also an increased risk of thrombosis, in turn significantly increasing the likelihood of stroke.

One possible method for treating ventricular fibrillation or flutter is so-called catheter ablation. This method involves the insertion of an ablation catheter into the ventricle, to "burn" or "obliterate" the pathways of pathological origin there. This means that the tissue in this region is modified in such a way that (as scar tissue) it loses its conductivity. There are different options for destroying the tissue. One frequently adopted approach is ablation using high-frequency current, which is transmitted from the catheter tip to the endocardium (inner wall) of the ventricle. There are further options available for ablation, for example cold ablation, etc.

One problem with such ablation methods is that the myocardium or cardiac muscle is not of uniform thickness but its thickness varies locally and with each patient.

For example some patients, perhaps due to more or less intensive sporting activity, have a thinner myocardium, while other patients have a thicker cardiac muscle. Pathologies can also be present, in such a manner for example that where there is stenosis of the coronary arteries certain areas of the myocardium are supplied less efficiently, so the muscle mass reduces locally and the thickness of the myocardium therefore decreases. There are also local differences, with the myocardium being thinner for example at the apical tip of the heart than in the mid-ventricular or basal region.

The catheter output must therefore be varied in order to penetrate the full thickness of the myocardium. If the output is too low, it may be that pathological pathways in the epicardium, in other words in the outer regions of the myocardium, are not reached and the ablation is therefore unsuccessful. If catheter output is too high on the other hand, unnecessary scarring of the myocardial tissue may result and in some instances the pericardium or heart sac may even be damaged.

For these reasons ablation of the left cardiac muscle or myocardium is currently rarely undertaken, as there is a high probability that pathological pathways in the epicardium for example will not be reached. On the other hand ablation—as shown by examples from the treatment of atrial fibrillation or flutter—is fundamentally a better alternative than conservative treatment with drugs and/or pacemaker implantation.

When myocardial ablation is carried out today in the ventricular region, the physician carrying out the procedure does not know the thickness of the myocardium, which varies significantly, specifically in the relevant patient group. It is not possible to identify this thickness in the fluoroscopy image. The physician is therefore only able to use mean values to set the ablation output, with the result that the problems mentioned above arise. It is not possible to ensure optimal setting of output with such an estimation of the thickness of the myocardium and appropriate output.

SUMMARY OF THE INVENTION

The object of the invention is therefore to specify a method that is improved in this respect, which reliably allows determination of the optimal output of an ablation catheter.

To achieve this object according to the invention provision is made with a method of the type mentioned in the introduction for said method to contain the following steps:
   Creation of at least one at least three-dimensional image recording of an ablation region provided for the myocardial ablation using at least one image recording apparatus,
   At least partial segmentation of the recorded ablation region to obtain segmentation information using a computation apparatus,
   At least partial determination from the segmentation information of the location-dependent thickness of the myocardium in the ablation region by the computation apparatus and
   Determination of the optimal output of the ablation catheter, in particular by the computation apparatus or a separate computation apparatus of an ablation catheter system, as a function of the determined myocardium thickness.

According to the invention therefore the output of the ablation catheter is no longer estimated using mean values but the appropriate output is determined based on a myocardium thickness determined (exactly) at a precise location.

To this end in the context of the inventive method at least one three-dimensional image recording of at least one ablation region provided for the myocardial ablation is first created. To this end an image recording apparatus is used, which is configured to record such three-dimensional image data, for example a computed tomograph or a magnetic resonance apparatus or an ultrasound apparatus, etc.

Segmentation is then carried out for the three-dimensional image recording or a plurality of image recordings, which at least partially show the region in the body of the patient of relevance to the ablation procedure, in other words for example the entire left ventricle or a sub-region of a ventricle. This segmentation is an image processing operation, which is carried out by a computation apparatus, in some instances using appropriate software or a software package. During segmentation regions with related content (in respect of data information) are generated in that corresponding image data regions (pixels or voxels) are combined according to specific homogeneity criteria. As a result different anatomical regions can be differentiated and/or assigned in the three-dimensional image recording.

The segmentation information obtained as a result of segmentation is used to determine the thickness of the myocardium in the ablation region and/or in a sub-region of the image recording or the region of relevance for the ablation as a function of location. By disassembling the image data recording and/or assigning the data in respect of the different anatomical structures it is therefore possible to calculate the actual thickness for specific locations in the myocardium of the respective patient. This is done for example by determining the distance between the endocardium and the epicardium, in other words the innermost layer of the cardiac wall and the outermost layer of the cardiac wall, as a function of location. In between is the cardiac tissue, so the thickness of the myocardium is indicated correspondingly by this distance.

This locally determined myocardium thickness is then used to determine the output of the ablation catheter in an optimal manner. This can be carried out by the computation apparatus, which in some instances has appropriate software or access to such for this purpose. The computation apparatus has access for this purpose to information, for example in a database, relating to the output required for the penetration of which tissue thickness. The computation apparatus can thus relate the myocardium thickness, which is now known locally, to the required output of the ablation catheter or create a link accordingly. In some instances location information relating to the position of the ablation catheter is used for this.

Output can also be determined by a separate computation apparatus, which is assigned to an ablation catheter system. This computation apparatus is thus part of the ablation catheter system and accordingly receives the determined location-dependent thickness of the myocardium from the (first) computation apparatus by way of a data connection, in order then to calculate the required output and in some instances to activate the ablation catheter of the ablation catheter system appropriately. The two computation apparatuses can of course also be integrated in one device.

Since according to the invention the myocardium thickness is no longer estimated but is determined locally in a precise manner, it is then possible to achieve an optimal ablation result by an optimal setting of the ablation output. Such an optimal ablation output is present, when the myocardium is penetrated completely, in other words all the pathological pathways are destroyed, while at the same time the minimum damage possible to healthy tissue is ensured.

It is thus possible, with knowledge of the thickness of the myocardium, in some instances at the current position of the ablation catheter, to determine the output of the latter optimally point by point and where necessary to set it accordingly. This protects healthy tissue, since it is ablated with optimal and not excessive output. The success rate for an ablation intervention is increased, since the likelihood of not reaching pathological neuron pathways in the epicardium is minimized.

The increased success rate and the further relevant factors of the invention also mean that interventions can be carried out more quickly and reliably, reducing costs and increasing the profit of the service provider. A successful ablation also significantly reduces the likelihood of a subsequent stroke due to thrombosis. It is also possible to dispense with conservative therapeutic measures, such as expensive drugs or pacemakers, so that not only are costs reduced but it is also possible to enhance the quality of a patient's life significantly. The inventive output determination, being a determination of technical data for a device setting, is a purely technical process, which is independent of the deployment of medical personnel. Nevertheless it is of course possible for the physician to edit the segmentation or determination and/or setting of the ablation output manually.

According to the invention as part of the segmentation it is possible for an operator to segment endocardium and epicardium contours of the ablation regions in particular automatically and/or manually. Manual segmentation can be provided in support of automatic (additional) editing. The pixels and/or voxels of the three-dimensional recordings are therefore allocated or assigned to the endocardium or epicardium. These are the two layers which surround the cardiac muscle system, in other words the myocardium. The endocardium and epicardium therefore so to speak represent the opposite boundaries or the inner and outer surfaces of the myocardium.

The thickness of the myocardium can then be determined using the distance between the endocardium and epicardium contours. This can be done for example by determining equidistant points or lines for example, which are located on the endocardium or epicardium or connect points on the two structures. Similarly radiating lines can be defined from an inner ventricle region, which run respectively from the endocardium to the epicardium. These then intersect the endocardium and epicardium respectively at one point, so that an associated local (in other words of relevance to this myocardium region) thickness of the myocardium results from the distance between these two points.

It should be ensured here during segmentation that the distance or myocardium thickness is determined in a sufficiently localized manner so that the output of the ablation catheter for the corresponding region can be set with sufficient accuracy.

In the case of a separate computation apparatus of the ablation catheter system the determined thickness of the myocardium in the ablation region can be transmitted, in particular automatically by the (first) computation apparatus, to the computation apparatus of the ablation catheter system, in particular to a computation apparatus for controlling a navigation system of the ablation catheter system. It should be noted here that the splitting of the computation apparatuses is possible but is in principle not necessary.

The instance should be considered here where a separate ablation catheter system is present with its own computation apparatus (in addition to the first computation apparatus for the thickness determination). In this instance the thickness of the myocardium, which was determined by the first computation apparatus, in other words not the computation apparatus of the ablation catheter system, is transmitted to the computation apparatus of the ablation catheter system. A data transmission therefore takes place between the two computation apparatuses. This can happen automatically with the aid of software configured appropriately for this purpose. After transmission the locally precisely determined myocardium thickness is available to the computation apparatus of the ablation catheter system, which then uses it to control the ablation catheter and/or to set its output and/or when controlling a navigation system for the catheter. Information about the current (location-dependent) thickness of the myocardium and therefore the optimal ablation output to be set is requested from the control computer of the ablation catheter systems or is transmitted by the above-mentioned computation apparatus to this. Together with the location information of the catheter, which is supplied for example by the navigation system of the ablation catheter system, it is possible to determine or calculate the required ablation output for all relevant locations or for the current catheter position from the thickness information.

The computation apparatus can generate at least one representation of an endocardial surface in the ablation region from the segmentation information and display it in particular on a screen and in some instances transmit it to a separate computation apparatus of the ablation catheter system. Of course representations can also be generated from the segmentation information, which show other information or anatomical regions, for example a sectional representation of the epicardium through the ventricle etc.

A representation of the endocardial surface is however recommended, as it provides a view of the or a region to be treated or the ventricle, which on the one hand allows an intuitive acquisition of the anatomy while on the other hand the surface representation can be used at the same time to show the required depth information by corresponding coding.

The representation is expediently displayed for viewing on a screen, for example a monitor or a flat screen or a monitor wall, etc. In some instances the representation can be transmitted in an appropriate data format to a separate computation apparatus of the ablation catheter system, where it is displayed on a screen as required. To this end the representation is sent by way of a data connection from the first computation apparatus to the computation apparatus of the ablation catheter system, in order to generate a screen representation there or only there.

The total location-dependent thickness of the myocardium at any point of the representation of the endocardial surface can expediently be stored. The myocardium thickness is obtained as the distance between the endocardium and epicardium, so that the associated thickness for example precisely in the region of a point (according to a line through the myocardium, on which this point is located) or a mean value of the thickness in the region around said point can be assigned to each point or at least to a sufficiently large number of points (pixels, voxels).

In the at least one representation of the endocardial surface the thickness of the myocardium can be represented, in particular overlaid, as depth information, in particular by color coding the surface.

It is therefore possible to generate a surface representation or a number of surface representations, which are lined up next to each other or can be called up one after the other, etc., in which the depth information is represented directly. This can be achieved for example by specific coding. Such a coding can be a color coding for example, which is overlaid on the anatomical information of the endocardial surface. A specific color then represents a specific thickness. It is also possible to represent the thickness of the myocardium in such a manner that it is displayed, if an operator moves a mouse pointer or another screen representation of an operating tool over said surface or requests that the depth information be displayed by clicking the mouse on it, etc.

For fast acquisition of the depth, in particular from a qualitative point of view, a color coding is recommended such that regions with a thin myocardium are colored red for example, while regions with a greater myocardium thickness are shown as blue. Intermediate regions can be marked accordingly with transition colors. This means that the very significant variations in myocardium thickness, which can be between 0.4 cm and 2 cm in individual instances in one region, can be quickly acquired. Information about the different myocardium thicknesses is therefore displayed directly to an operator or the ablation catheter system. This information is extremely important, since successful ablation can only be achieved even with normal fluctuations in thickness in the region of around 0.8 cm to 1.4 cm, if catheter output is actually tailored precisely to these thickness differences.

When the surface with myocardium thickness coding is transmitted to a catheter navigation system or an ablation catheter system, this system can access the thickness information for the myocardium at the points of the surface directly. The color-coded representation or the representation coded otherwise in respect of depth information then only serves as a visualization of the quantitatively available thickness information for an operator for example.

The location-dependent thickness of the myocardium in the ablation region and/or in some instances a representation of the endocardial surface can be registered with at least one current position information item of the ablation region, in particular by the computation apparatus or in some instances a computation apparatus of the ablation catheter system and/or by means of current image recordings of the ablation region. Of course only one integrated computation apparatus may also be provided. Registration of the surface model with current position information for the ventricle allows assignment of the depth information to the region currently of importance for the treatment or the region acquired by this. The thickness information, which was obtained for example by means of a computed tomography scan obtained one or two days before the actual ablation, can thus be compared with the current position of the ventricle. This ensures that the locally correct thickness information is used for the ablation.

The specified optimal output of the ablation catheter can be set manually (by editing) and/or automatically, in particular by the computation apparatus or in some instances a computation apparatus of the ablation catheter system. A (preferred) automatic setting can be checked for example manually by an operator and in some instances adjusted. The calculated or determined output of the ablation catheter, which produces optimal results, on the other hand is set without further intervention by an operator, for example by the first computation apparatus or by a further computation apparatus of an ablation catheter system, to which this information was transmitted. In this instance the output information is converted directly to activation of the ablation catheter system or the ablation catheter. Output is optimally tailored in such a manner that the thicker the myocardium, the higher the selected ablation output. Information about the thickness of the myocardium at the present treatment or catheter position and thus the optimal ablation output to be set can then be drawn by the separate computation apparatus as the control computer for ablation output from the location information of the catheter on the one hand and the thickness-coded endocardial surface on the other hand. Manual setting or editing can take place as an alternative or in support.

The output of the ablation catheter can correspondingly be set as a function of current location information for the ablation catheter, in particular as a function of current location information of a navigation system of the ablation catheter system. In this instance the ablation catheter has a navigation apparatus, which determines the current location of the catheter in the anatomy. The navigation system is also used to modify or control the position or location of the catheter in the anatomy, so that current location information is available correspondingly for the navigation system or through the navigation system and can be compared with the thickness information for example from the representation of the endocardial surface.

The image recording apparatus used to create the at least one at least three-dimensional image recording can be a computed tomography apparatus and/or a magnetic resonance apparatus and/or a rotation angiography apparatus and/or an ultrasound apparatus. Other imaging techniques not mentioned here can also be used, which similarly allow the creation of three or multi-dimensional image recordings, for example from films of three-dimensional images. It is important that one at least three-dimensional recording of the heart or left myocardium is possible. It is also possible for the three-dimensional image recordings or multi-dimensional image recordings to be combined or merged from individual recordings using different imaging techniques, so that further information from another technique can be included in magnetic resonance images for example, to improve image quality.

The invention also relates to a medical apparatus, configured to determine an optimal output of an ablation catheter for a myocardial ablation in a patient, in particular according to a method as claimed in one of the preceding claims, in some instance with at least one image recording apparatus for creating at least one at least three-dimensional image recording of an ablation region provided for the myocardial ablation, with a computation apparatus, configured for at least partial segmentation of the ablation region recorded using the or an image recording apparatus to obtain segmentation information and for the at least partial determination of the location-dependent thickness of the myocardium in the ablation region from the segmentation information and in some instances with a separate computation apparatus of an ablation catheter system of the medical apparatus, with the computation apparatus or in some instances the separate computation apparatus being configured to determine the optimal output of the ablation catheter as a function of the determined myocardium thickness. The medical apparatus is thus configured to determine the optimal output of an ablation catheter for a myocardial ablation in a patient, to ensure a successful ablation as a result.

To this end the medical apparatus has a computation apparatus, with which it is possible to segment an ablation region recorded by means of the or an image recording apparatus in some instances using suitable program means. Segmentation allows the computation apparatus to acquire segmentation information, from which the computation apparatus in turn determines the location-dependent thickness of the myocardium in the ablation region.

The medical apparatus can also have one or more image recording apparatuses, which can be used to create the three-dimensional or multi-dimensional image recordings. An ablation catheter or ablation catheter system can also be part of the medical apparatus. In this instance the thickness information is expediently transmitted from the computation apparatus to the ablation catheter system or to a separate computation apparatus, which has such, whereupon the ablation output of the ablation catheter is set correspondingly in an automatic manner.

According to the invention it is thus ensured that ablation is carried out in each instance with optimal output, so that on the one hand healthy tissue is protected and on the other hand pathological neuron pathways in the epicardium are also reached.

BRIEF DESCRIPTION OF THE DRAWINGS

Further advantages, features and details of the invention will emerge from the exemplary embodiments that follow and from the drawings, in which.

DETAILED DESCRIPTION OF THE INVENTION

Figure 1:
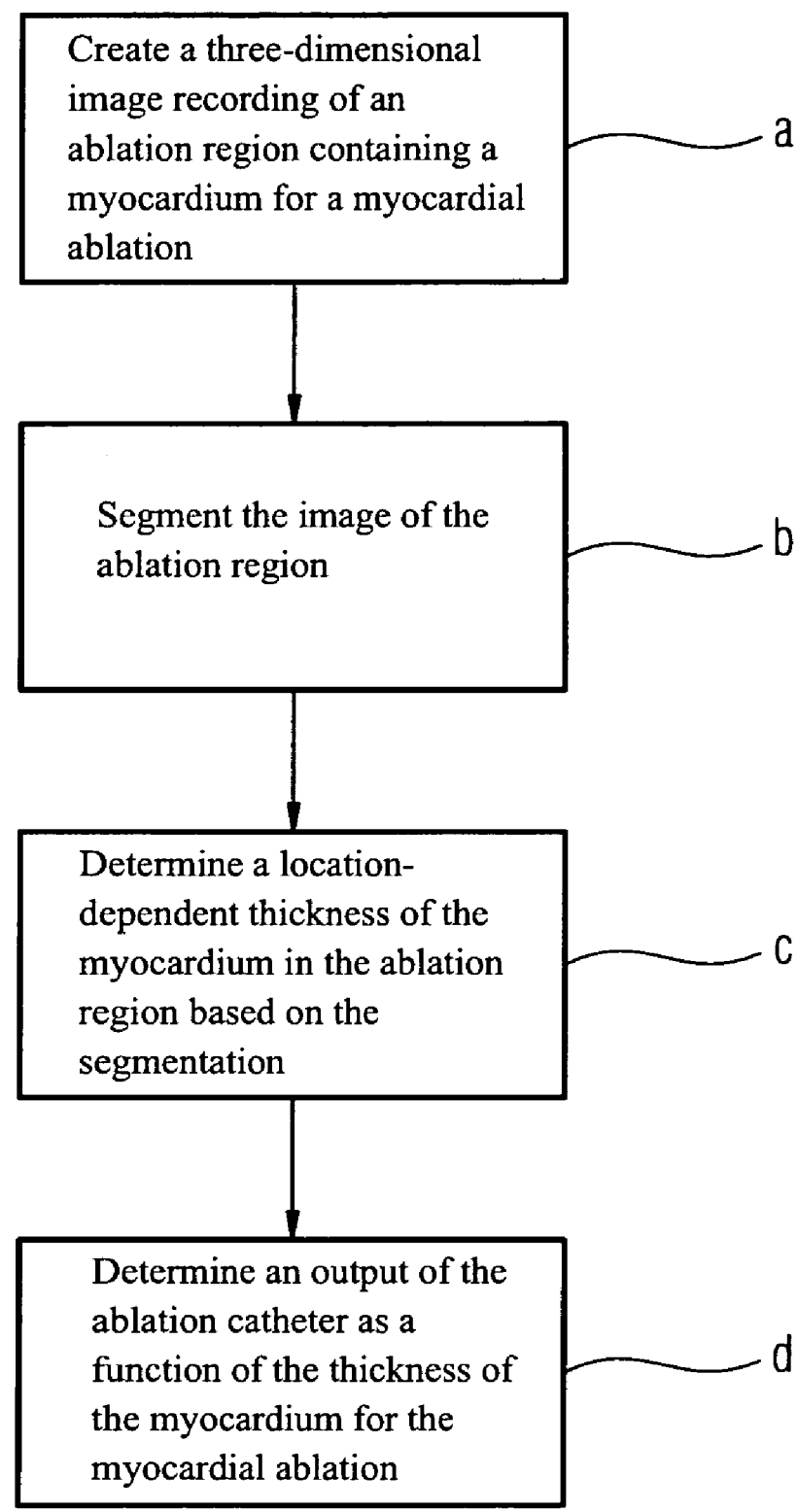
FIG. 1 shows an outline of the sequence of an inventive method.

FIG. 1 shows an outline of the sequence of an inventive method.

According to step a at least one at least three-dimensional image recording is first created of at least one ablation region provided for the myocardial ablation, in other words for example of a left ventricle of a patient, with the aid of an image recording apparatus or a number of image recording apparatuses, such as a computed tomograph or a magnetic resonance apparatus. Images can likewise be created as part of rotation angiography or using ultrasound.

Then according to step b an at least partial segmentation of the image recordings or of the recorded ablation region is carried out. Segmentation, in other words the division of the content, allows segmentation information to be obtained, with segmentation being carried out by a computation apparatus, in some instances with appropriate software means.

In step c the segmentation information is used to calculate the location-dependent thickness of the myocardium in the ablation region at least partially, in other words for the region of the present segmentation information or for a sub-region, for which segmentation information was determined. This is done again by the computation apparatus.

In step d the optimal output of the ablation catheter is determined. This can be done again by the first-mentioned computation apparatus or, after corresponding transmission of the thickness information, which was obtained in step c, by a separate computation apparatus of an ablation catheter system. Accordingly the first computation apparatus or a separate computation apparatus can then set the ablation output in an appropriate manner directly at the catheter during a subsequent activation process (not shown here). This can be done automatically.

Figure 2:
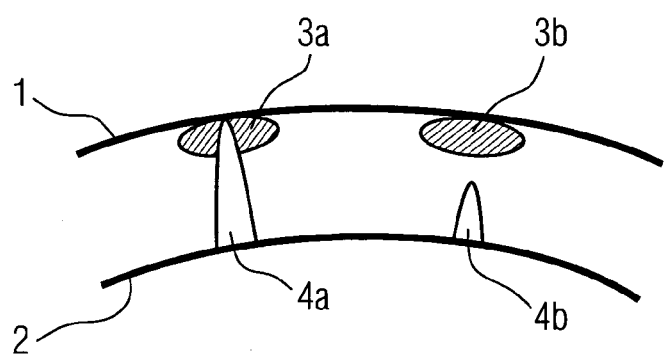
FIG. 2 shows a representation of the effects of different ablation outputs.

FIG. 2 shows a representation of the effects of different ablation outputs for a ventricle-myocardium ablation. It shows both the epicardium 1 and the endocardium 2. The outer epicardium 1 and the inner endocardium 2 form the limits of the cardiac muscle system or surround the myocardium.

FIG. 2 also shows examples of possible pathological pathways 3a and 3b.

Setting different ablation outputs results in different penetration depths into the myocardium, shown here as penetration depths 4a and 4b. Penetration depth 4a here indicates a penetration depth with a high ablation output, while 4b indicates a penetration depth with a low ablation output. The penetration depth 4b is so small that the pathological pathway 3b is not reached and therefore cannot be destroyed. In this instance the myocardium ablation carried out is unsuccessful due to the incorrect setting of the ablation output of the catheter. On the other hand, if the penetration depth 4a was selected as rather greater than shown here, in other words was too great, it would be possible that healthy tissue or the pericardium surrounding the heart might be damaged.

The inventive optimal determination of the ablation output allows such errors to be prevented.

The inventive method hereby relates exclusively to the determination of the optimal output, in other words the link between the thickness information and the technical (output) data, which determines the setting of the catheter, in some instances also to the point of catheter activation. The treatment as such, in other words the execution of the ablation, is not the subject matter of the invention.

Figure 3:
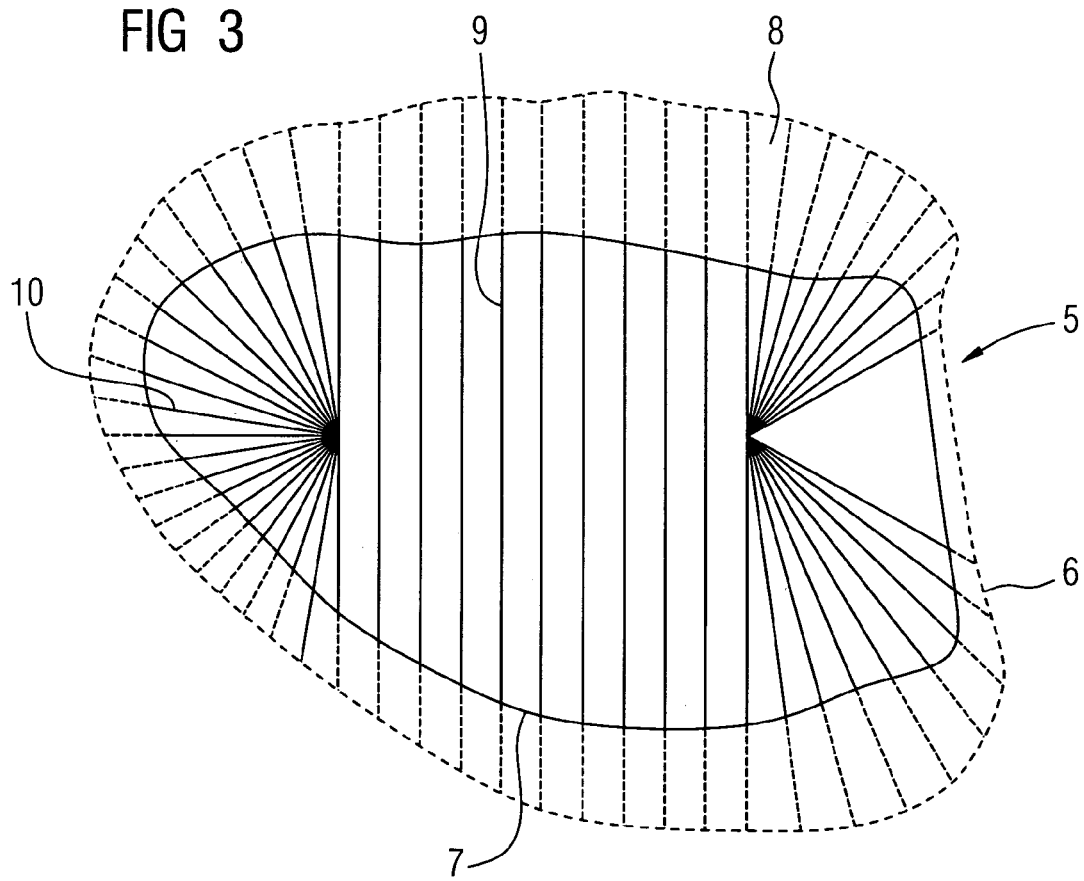
FIG. 3 shows an outline for segmentation according to an inventive method.

FIG. 3 shows an outline for segmentation according to an inventive method. It shows a section through a longitudinal axis 5 with segmented endocardium contours 7, shown here with a broken line and segmented epicardium contours 6. Between the segmented endocardium contours 7 and the epicardium contours 6 is the myocardium 8. The thickness of the myocardium 8 thus results from the distance between the endocardium contours 7 and the epicardium contours 6. The distance is obtained for example from the equidistant lines 9 shown here and the radiating lines 10 in the left and right end regions of the diagram, each of which runs (in one or both end regions of the line) through the endocardium contour 7 to the epicardium contour 6, thereby connecting two points of the respective endocardium contour 7 and epicardium contour 6 together, providing distance information. Of course other line guides (e.g. non-equidistant lines) can also be used.

The segmentation information can thus be used directly to determine the thickness of the myocardium 8 as described in a location-dependent manner, in other words for the myocardium 8 between the respective points of the endocardium contour 7 and/or the epicardium contour 6.

Figure 4:
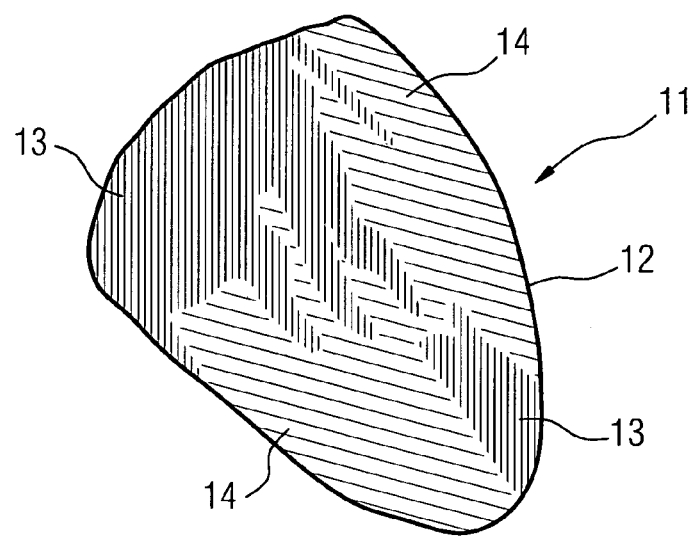
FIG. 4 shows a representation of an endocardial surface according to the invention and FIG. 5 shows an inventive medical apparatus.

FIG. 4 shows a representation 11 of an endocardial surface 12 according to the invention. The endocardial surface 12 is color-coded, as shown here by corresponding hatching. In the region of hatching 13, which is for example coded blue in an actual representation 11, the myocardium is relatively thick, while in the region of hatching 14 the myocardium is thinner, being of a thickness, which varies overall for example between 0.8 cm and 1.3 cm. These transitions are fluid. The thin region of the hatching 14 can be color-coded red. Transition regions with a mean thickness are identified correspondingly by transition colors between blue and red. These are not shown in the present representation 11 for reasons of simplicity. The depth information can thus be visualized for an operator directly as color coding or other coding, for example by the actual use of hatching as shown here. This allows optimal intuitive acquisition of information.

With the representation 11 the myocardium thickness information from the distance between the endocardium and epicardium is stored respectively for the individual points of the endocardial surface 12 in a computation apparatus, for example the computation apparatus of the ablation catheter system, so that it is available for activation of the catheter. To this end the endocardial surface 12 is registered with current position information of the ventricle provided for the ablation, to ensure that the thickness information is converted correctly to location-dependent activation of the catheter.

Figure 5:
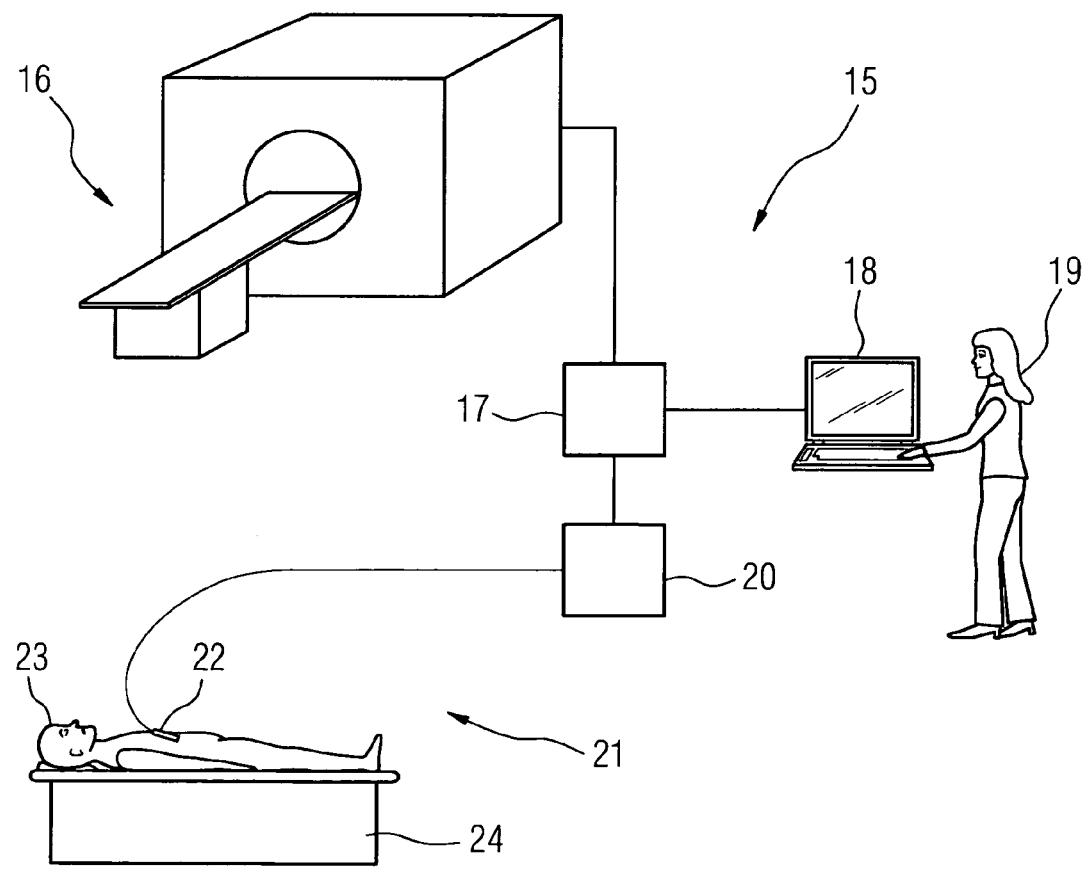

FIG. 5 shows an inventive medical apparatus 15, configured with an image recording apparatus 16 for creating at least three-dimensional image recordings of an ablation region provided for a myocardial ablation. The data from the image recording apparatus 16 is forwarded by way of a data connection to a computation apparatus 17, which also has a screen 18 for visualization or operation by an operator 19.

The computation apparatus 17 carries out image processing of the images from the image recording apparatus 16, by segmenting these, among other things to assign structures. The segmentation here relates to endocardial structures and epicardial structures, whose distance at specific positions of the image recording from the image recording apparatus 16 gives the local myocardium thickness. The computation apparatus 17 uses program means correspondingly to determine the location-dependent thickness of a myocardium in the ablation region from the segmentation information.

This thickness information is transmitted by the computation apparatus 17 to a separate computation apparatus 20 of an ablation catheter system 21 with the ablation catheter 22. The transmission here takes place as a function of a corresponding input by the operator 19.

Alternatively transmission to the separate computation apparatus 20 can take place fully automatically. The separate computation apparatus 20 uses the thickness information relating to the myocardium to determine the optimal output of the ablation catheter 22 in such a manner that ablation can be carried out with an output that is neither too low nor too high. To this end the separate computation apparatus 20 carries out a registration beforehand with current position information for the ablation catheter 22 of the ablation catheter system 21.

Alternatively the required output can be determined generally beforehand for all or a sufficient number of points on the image recording from the image recording apparatus 16, so that registration with the current position can be carried out later during the execution of the actual ablation on the patient 23 on the patient support 24.

It is thus possible with the inventive method and/or the inventive medical apparatus to determine the ablation output optimally in such a manner that during the actual ablation pathological regions are reached and at the same time no healthy tissue is damaged unnecessarily. The determination method of the invention thus replaces the estimation of the thickness of the myocardium used until now, for example based on a brief glance at a computed tomography recording by the physician or simple orientation using mean values.

The invention claimed is:

1. A method for determining an optimal output of an ablation catheter for a myocardial ablation in a patient, comprising:
creating a three-dimensional image recording of an ablation region containing a myocardium for the myocardial ablation;
segmenting the image of the ablation region;
determining a location-dependent thickness of the myocardium in the ablation region based on the segmentation; and
determining the optimal output of the ablation catheter as a function of the thickness of the myocardium for performing the myocardial ablation.

2. The method as claimed in claim 1, wherein a contour of an endocardium and a contour of an epicardium in the obligation region are manually or automatically segmented in the segmentation.

3. The method as claimed in claim 2, wherein the thickness of the myocardium is determined based on a distance between the contour of the endocardium and the contour of the epicardium.

4. The method as claimed in claim 1, wherein the thickness of the myocardium is transmitted to a computer for controlling a navigation system of the ablation catheter.

5. The method as claimed in claim 1, wherein a representation of an endocardial surface in the ablation region is generated based on the segmentation.

6. The method as claimed in claim 5, wherein the representation of the endocardial surface is displayed on a screen.

7. The method as claimed in claim 6, wherein the thickness of the myocardium is stored for each point on the representation of the endocardial surface.

8. The method as claimed in claim 6, wherein the thickness of the myocardium is overlaid in the representation of the endocardial surface.

9. The method as claimed in claim 8, wherein the thickness of the myocardium is overlaid in the representation of the endocardial surface by color-coding the endocardial surface.

10. The method as claimed in claim 5, wherein the representation of the endocardial surface is registered with a current position of the ablation catheter.

11. The method as claimed in claim 1, wherein the thickness of the myocardium is registered with a current position of the ablation catheter.

12. The method as claimed in claim 1, wherein the output of the ablation catheter is set manually or automatically after the determination.

13. The method as claimed in claim 1, wherein the output of the ablation catheter is set as a function of a current position of the ablation catheter after the determination.

14. A medical apparatus for determining an optimal output of an ablation catheter for a myocardial ablation in a patient, comprising:
- an image recording apparatus that recodes a three-dimensional image recording of an ablation region containing a myocardium for the myocardial ablation; and
- a computer that:
    - segments the image of the ablation region,
    - determines a location-dependent thickness of the myocardium in the ablation region based on the segmentation, and
    - determines the optimal output of the ablation catheter as a function of the thickness of the myocardium for performing the myocardial ablation.

15. The medical apparatus as claimed in claim 14, wherein the image recording apparatus is selected from the group consisting of: a computed tomography apparatus, a magnetic resonance apparatus, a rotation angiography apparatus, and an ultrasound apparatus.

* * * * *